(12) United States Patent
Squire-Smith

(10) Patent No.: US 11,389,573 B2
(45) Date of Patent: Jul. 19, 2022

(54) EAR WATER SUCTION APPARATUS

(71) Applicant: Tristan Squire-Smith, London (CA)

(72) Inventor: Tristan Squire-Smith, London (CA)

( * ) Notice: Subject to any disclaimer, the term of this patent is extended or adjusted under 35 U.S.C. 154(b) by 591 days.

(21) Appl. No.: 16/437,904

(22) Filed: Jun. 11, 2019

(65) Prior Publication Data

US 2020/0390946 A1 Dec. 17, 2020

(51) Int. Cl.
*A61M 39/08* (2006.01)
*A61M 1/00* (2006.01)

(52) U.S. Cl.
CPC ............ *A61M 1/0023* (2013.01); *A61M 1/90* (2021.05); *A61M 39/08* (2013.01); *A61M 2205/076* (2013.01); *A61M 2210/0662* (2013.01)

(58) Field of Classification Search
CPC ...... A61M 1/0023; A61M 1/90; A61M 39/08; A61M 2205/076; A61M 2210/0662
See application file for complete search history.

(56) References Cited

U.S. PATENT DOCUMENTS

| | | | |
|---|---|---|---|
| 4,896,679 A * | 1/1990 | St. Pierre | A61F 11/10 128/868 |
| 5,868,139 A | 2/1999 | Zeece | |
| 5,979,072 A | 11/1999 | Collins, II | |
| 6,059,803 A | 5/2000 | Spilman | |
| 6,725,568 B2 | 4/2004 | Gronka | |
| 6,991,638 B2 | 1/2006 | Wang | |
| 10,149,037 B1 * | 12/2018 | Chen | H04R 1/105 |
| 2003/0047376 A1 * | 3/2003 | Oster | A61B 7/02 181/131 |
| 2007/0100300 A1 * | 5/2007 | Hashemian | A61F 11/202 604/275 |
| 2009/0139520 A1 * | 6/2009 | Weaver | A61M 15/025 128/203.12 |

FOREIGN PATENT DOCUMENTS

FR 2728469 A1 * 6/1996 .......... A61M 1/0001

OTHER PUBLICATIONS

FR 2728469 English Translation (Year: 1996).*

* cited by examiner

*Primary Examiner* — Philip R Wiest
*Assistant Examiner* — Gregory J Feulner

(57) ABSTRACT

An aural water removal suction apparatus for removing water from within ears includes a mouthpiece that has a principal opening extending into a mouth portion and a stem aperture extending from the principal opening through a stem portion. A tubing is coupled to the mouthpiece. A pair of ear tubes comprising a right ear tube and a left ear tube is coupled to the tubing. A pair of ear buds that is configured to be inserted into a user's ears is coupled to the pair of ear tubes. The canal aperture of each of the pair of ear buds, the pair of ear tubes, the tubing, and the stem aperture of the mouthpiece are all in fluid communication. The user creates suction through the canal aperture of the pair of ear buds with her mouth on the principal opening of the mouthpiece to draw water from her ears.

8 Claims, 4 Drawing Sheets

EAR WATER SUCTION APPARATUS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to aural water removal devices and more particularly pertains to a new aural water removal device for removing water from within ears.

BRIEF SUMMARY OF THE INVENTION

An embodiment of the disclosure meets the needs presented above by generally comprising a mouthpiece that has a principal opening extending into a mouth portion and a stem aperture extending from the principal opening through a stem portion. A tubing that has a connector portion and a bifurcated portion comprising a right branch and a left branch is coupled to the mouthpiece. A distal end of the connector portion is coupled around the stem portion of the mouthpiece. A pair of ear tubes comprising a right ear tube and a left ear tube coupled to the right branch and the left branch, respectively, is coupled to the tubing. A pair of ear buds comprising a right bud and a left bud each having a canal aperture coupled around an ear end of the right ear tube and the left ear tube, respectively, is coupled to the pair of ear tubes. The pair of ear buds is configured to be inserted within a user's ears. The canal aperture of each of the pair of ear buds, the pair of ear tubes, the tubing, and the stem aperture of the mouthpiece are all in fluid communication. The user thus is able to create suction through the canal aperture of each of the pair of ear buds with her mouth on the principal opening of the mouthpiece to draw water from her ears.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
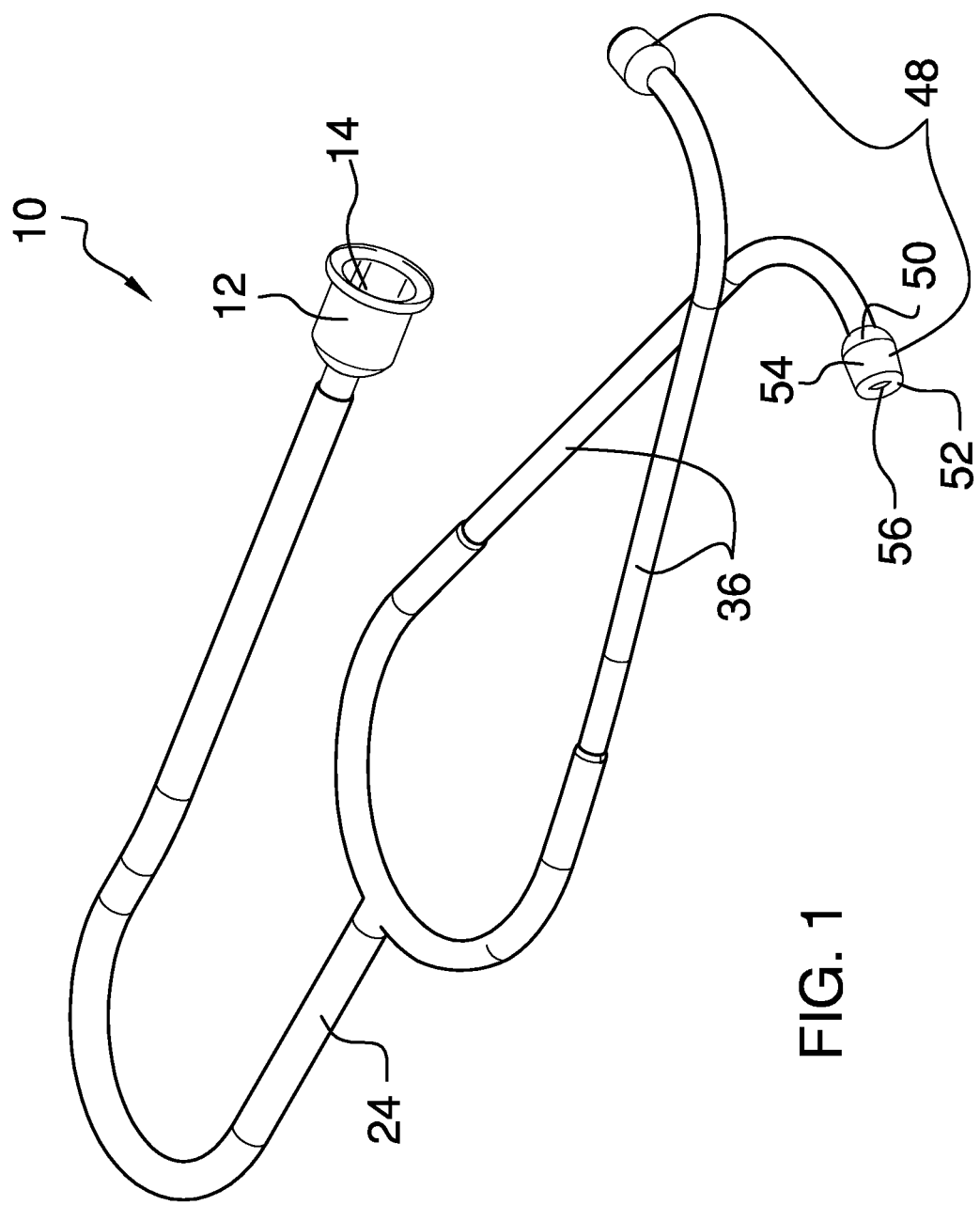
FIG. 1 is an isometric view of an aural water removal suction apparatus according to an embodiment of the disclosure.
Figure 2:
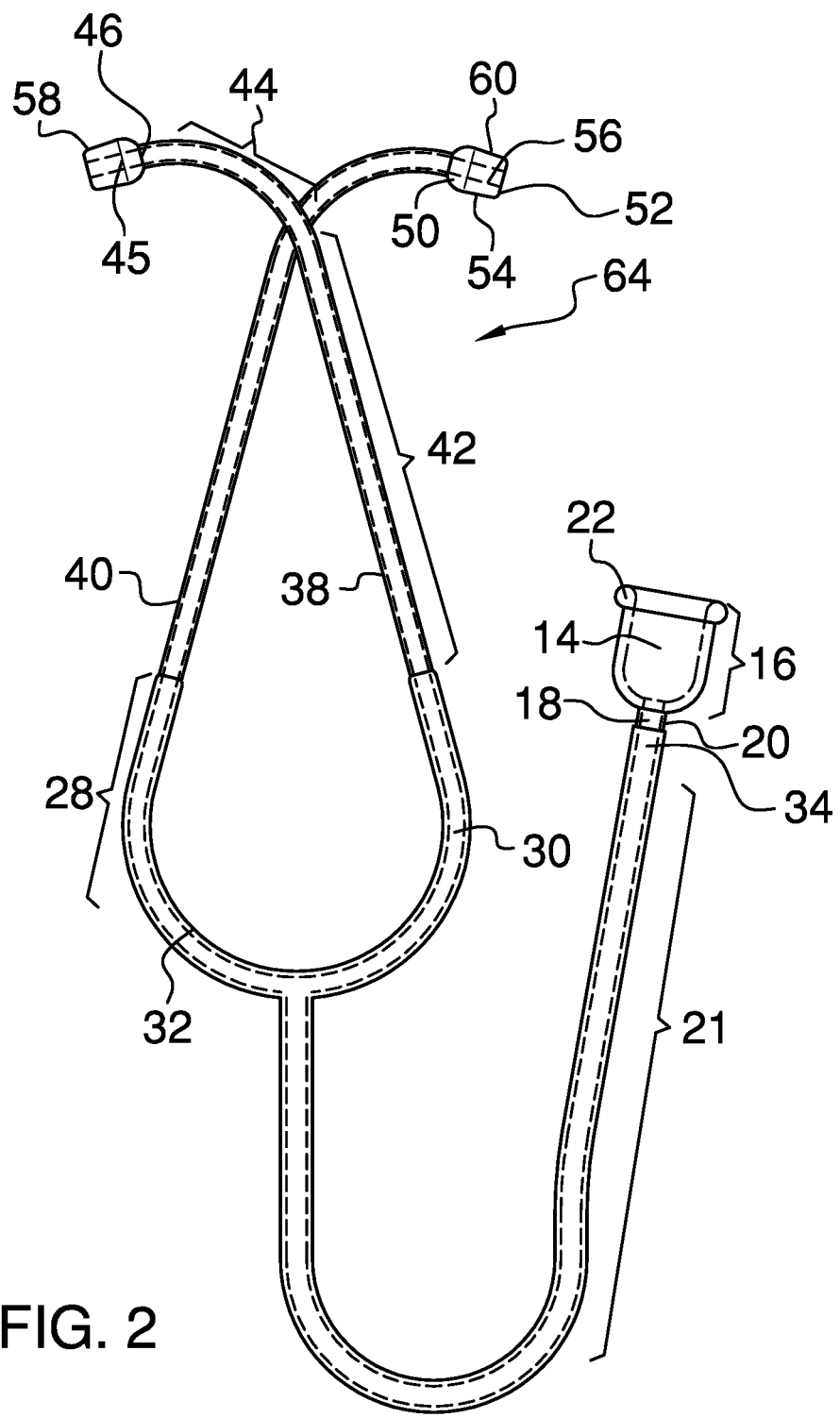
FIG. 2 is a bottom plan view of an embodiment of the disclosure.
Figure 3:
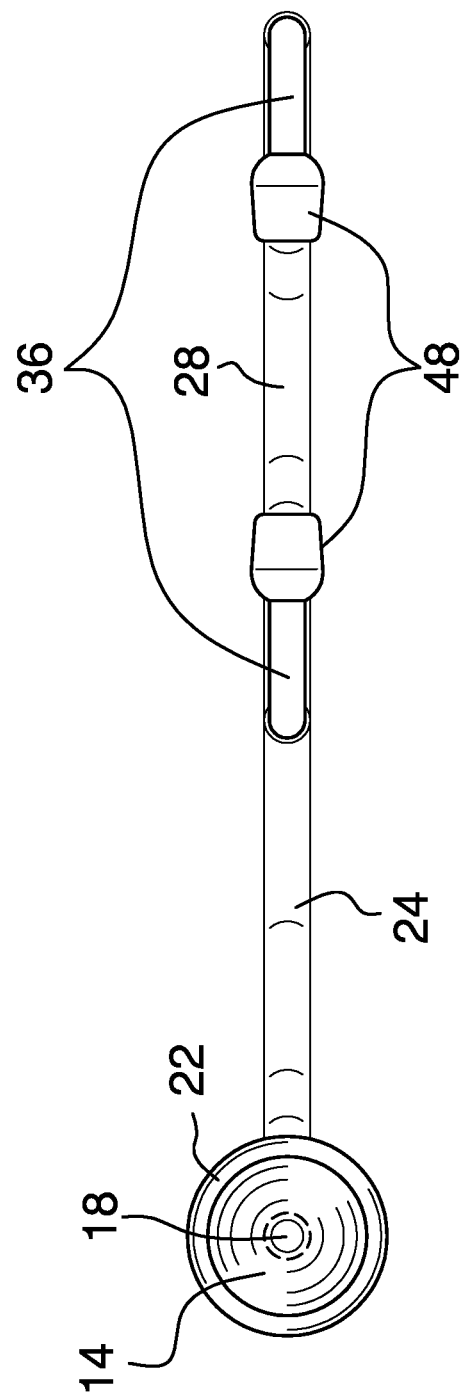
FIG. 3 is a front elevation view of an embodiment of the disclosure.
Figure 4:
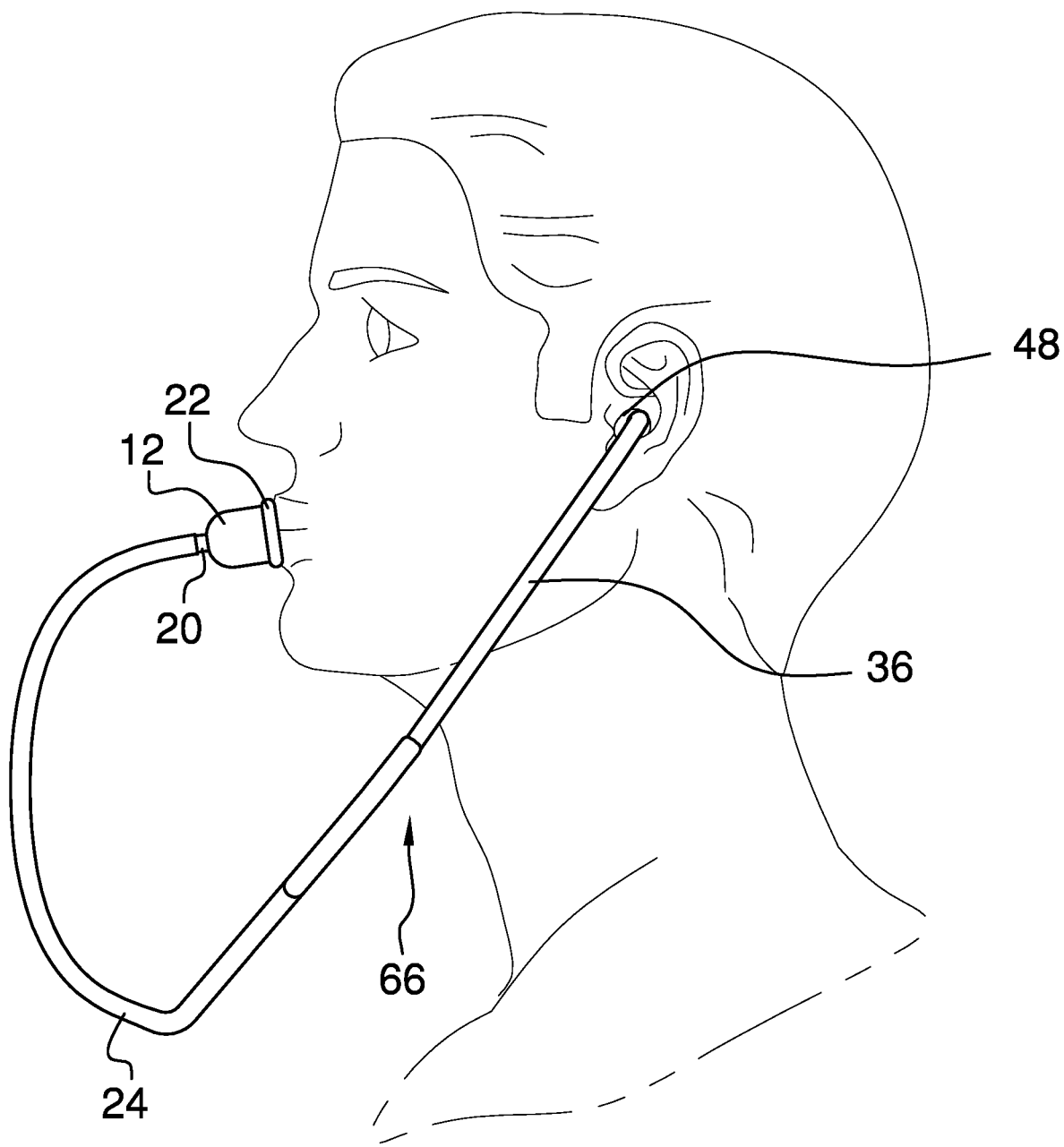
FIG. 4 is an in-use view of an embodiment of the disclosure.

With reference now to the drawings, and in particular to FIGS. 1 through 4 thereof, a new aural water removal device embodying the principles and concepts of an embodiment of the disclosure and generally designated by the reference numeral 10 will be described.

As best illustrated in FIGS. 1 through 4, the aural water removal suction apparatus 10 generally comprises a mouthpiece 12 that has a principal opening 14 extending into a cup-shaped mouth portion 16 and a stem aperture 18 extending from the principal opening 14 through a stem portion 20. The principal opening 14 of the mouthpiece 12 has a rounded lip 22 continuously extending around a perimeter thereof. A tubing 24 that has a connector portion 21 and a horseshoe-shaped bifurcated portion 28 comprising a right branch 30 and a left branch 32 is coupled to the mouthpiece 12. A distal end 34 of the connector portion 21 is coupled around the stem portion 20 of the mouthpiece 12. A pair of ear tubes 36 comprising a right ear tube 38 and a left ear tube 40 is coupled to the right branch 30 and the left branch 32 of the tubing 24, respectively. Each of the ear tubes 36 has a straight portion 42 partially coupled within the tubing 24 and a bent portion 44 orienting a thin portion 45 of an ear end 46 to lie perpendicular with the straight portion 42. A pair of ear buds 48 is coupled to the pair of ear tubes 36. Each of the ear buds 48 has a rounded back side 50, a front side 52, and a tapered side wall 54 extending therebetween. The pair of ear buds 48 comprises a right bud 58 and a left bud 60 each having a canal aperture 56 extending from the front side 52 through the back side 50. The canal aperture 56 of each of the right bud 58 and the left bud 60 is coupled around the thin portion 45 of the ear end of the right ear tube 38 and the left ear tube 40, respectively. The pair of ear buds 48 is configured to be inserted within a user's ears. The tubing 24 is flexible such that the pair of ear tubes 36 moves between a crossed position 64 and an alternative wear position 66. The bifurcated portion 28 is biased to return the ear tubes 36 to the crossed position 64. The ear tubes 36 thus apply pressure on the ear buds 48 within the user's ears in the wear position 66. The canal aperture 56 of each of the pair of ear buds 48, the pair of ear tubes 36, the tubing 24, and the stem aperture 20 of the mouthpiece 12 are all in fluid communication.

In use, the user is able to create suction through the canal aperture 56 of each of the pair of ear buds 48 with her mouth on the principal opening 14 of the mouthpiece 12 to draw water from her ears.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An aural water removal suction apparatus comprising:
   a mouthpiece, the mouthpiece having a principal opening extending into a mouth portion and a stem aperture extending from the principal opening through a stem portion;
   a tubing coupled to the mouthpiece, the tubing having a connector portion and a bifurcated portion comprising a right branch and a left branch, a distal end of the connector portion being coupled around the stem portion of the mouthpiece, the bifurcated portion being horseshoe-shaped, the connector portion extending perpendicularly from a junction with the bifurcated portion, the left branch and the right branch being in direct environmental communication with each other at the junction of the connector portion and the bifurcated portion, the tubing being flexible such that the pair of ear tubes moves between a crossed position and an alternative wear position, the bifurcated portion being biased to return the ear tubes to the crossed position, the ear tubes thus applying pressure on the ear buds within the user's ears in the use position;
   a pair of ear tubes coupled to the tubing, the pair of ear tubes comprising a right ear tube and a left ear tube coupled to the right branch and the left branch, respectively; and
   a pair of ear buds coupled to the pair of ear tubes, the pair of ear buds comprising a right bud and a left bud each having a canal aperture coupled around an ear end of the right ear tube and the left ear tube, respectively, the pair of ear buds being configured to be inserted within a user's ears;
   wherein the canal aperture of each of the pair of ear buds, the pair of ear tubes, the tubing, and the stem aperture of the mouthpiece are all in fluid communication, the user thus being able to create suction through the canal aperture of each of the pair of ear buds with her mouth on the principal opening of the mouthpiece to draw water from her ears.

2. The aural water removal suction apparatus of claim 1 further comprising each of the ear tubes having a straight portion and a bent portion, the bent portion orienting the ear end to lie perpendicular with the straight portion.

3. The aural water removal suction apparatus of claim 1 further comprising each of the ear buds having a rounded back side, a front side, and a tapered side wall extending therebetween, the canal aperture extending from the front side through the back side.

4. The aural water removal suction apparatus of claim 1 further comprising the right ear tube and the left ear tube being coupled within the right branch and the left branch, respectively.

5. The aural water removal suction apparatus of claim 1 further comprising the mouth portion of the mouthpiece being cup-shaped.

6. The aural water removal suction apparatus of claim 1 further comprising the principal opening of the mouthpiece having a rounded lip continuously extending around a perimeter thereof.

7. The aural water removal suction apparatus of claim 1 further comprising the ear end of each of the right ear tube and the left ear tube having a thin portion, the canal aperture of the pair of ear buds being selectively engageable around the thin portion, the ear buds thus being replaceable.

8. An aural water removal suction apparatus comprising:
   a mouthpiece, the mouthpiece having a principal opening extending into a cup-shaped mouth portion and a stem aperture extending from the principal opening through a stem portion, the principal opening of the mouthpiece having a rounded lip continuously extending around a perimeter thereof;
   a tubing coupled to the mouthpiece, the tubing having a connector portion and a horseshoe-shaped bifurcated portion comprising a right branch and a left branch, the connector portion extending perpendicularly from a junction with the bifurcated portion, a distal end of the connector portion being coupled around the stem portion of the mouthpiece;
   a pair of ear tubes coupled to the tubing, the pair of ear tubes comprising a right ear tube and a left ear tube coupled to the right branch and the left branch, respectively, each of the ear tubes having a straight portion partially coupled within the tubing and a bent portion, the bent portion orienting a thin portion of an ear end to lie perpendicular with the straight portion; and
   a pair of ear buds coupled to the pair of ear tubes, each of the ear buds having a rounded back side, a front side, and a tapered side wall extending therebetween, a canal aperture extending from the front side through the back side, the pair of ear buds comprising a right bud and a left bud each having the canal aperture coupled around the thin portion of the ear end of the right ear tube and the left ear tube, respectively, the pair of ear buds being configured to be inserted within a user's ears, the tubing being flexible such that the pair of ear tubes moves between a crossed position and an alternative wear position, the bifurcated portion being biased to return the ear tubes to the crossed position, the ear tubes thus applying pressure on the ear buds within the user's ears in the use position;

wherein the canal aperture of each of the pair of ear buds, the pair of ear tubes, the tubing, and the stem aperture of the mouthpiece are all in fluid communication, the user thus being able to create suction through the canal aperture of each of the pair of ear buds with her mouth on the principal opening of the mouthpiece to draw water from her ears.

\* \* \* \* \*